United States Patent [19]

Melaja et al.

[11] 4,075,406
[45] Feb. 21, 1978

[54] PROCESS FOR MAKING XYLOSE

[75] Inventors: Asko J. Melaja; Lauri Hamalainen, both of Kantvik, Finland

[73] Assignee: Suomen Sokeri Osakeyhtio, Helsinki, Finland

[21] Appl. No.: 608,706

[22] Filed: Aug. 28, 1975

Related U.S. Application Data

[63] Continuation of Ser. No. 463,037, April 22, 1974, abandoned, which is a continuation-in-part of Ser. No. 354,391, April 25, 1973, abandoned.

[51] Int. Cl.$^2$ .................... C07G 1/08; C07C 31/18; C13K 1/02; C13D 3/14
[52] U.S. Cl. ........................................ 536/1
[58] Field of Search .......... 260/209 R, 635 A, 635 C; 127/46, 37, 46 A, 46 B; 162/16; 536/1

[56] References Cited

U.S. PATENT DOCUMENTS

| | | | |
|---|---|---|---|
| 2,759,856 | 8/1956 | Saums et al. | 127/37 |
| 2,890,972 | 6/1959 | Wheaton | 127/46 |
| 3,305,395 | 2/1967 | Scallet et al. | 127/46 B |
| 3,420,709 | 1/1969 | Burretl et al. | 127/53 |
| 3,479,248 | 11/1969 | Nobile | 162/16 |
| 3,558,725 | 1/1971 | Kohno et al. | 260/635 C |
| 3,579,380 | 5/1971 | Friese | 260/635 C |
| 3,730,770 | 5/1973 | Zievers et al. | 127/46 A |
| 4,008,285 | 2/1977 | Melaja et al. | 536/1 |

Primary Examiner—Henry R. Jiles
Assistant Examiner—Cary Owen
Attorney, Agent, or Firm—Brumbaugh, Graves, Donohue & Raymond

[57] ABSTRACT

A method for recovering xylose from pentosan-, preferably xylan-containing raw materials including the steps of hydrolyzing the raw material, purifying the hydrolysate by ion exclusion and color removal, and then subjecting the purified solution to chromatographic fractionation to provide a solution containing a high level of xylose.

5 Claims, 3 Drawing Figures

FOUR PROCEDURES FOR PENTOSE SUGAR SOLUTION FINAL PURIFICATION AND COLOR REMOVAL

PROCESS FOR MAKING XYLOSE

This application is a continuation application of our copending application Ser. No. 463,037, filed Apr. 22, 1974, now abandoned, which was a continuation-in-part of our copending application Ser. No. 354,391, filed Apr. 25, 1973, now abandoned.

This invention relates to a process for obtaining xylose from pentosan-containing materials, preferably xylan-containing materials by acid hydrolysis of the materials followed by purifying and chromatographic separation techniques.

The prior art is replete with processes described as being suitable for obtaining xylose from natural products such as birch wood, corn cobs, cotton seed hulls and the like. The Russian article by Leihin, E. R. and Soboleva, G. D., Proizvostro Ksilita (Production of Xylitol) Moscow, 1962 gives a review of the processes known at that time.

Recent United States patents dealing with the subject include U.S. Pat. Nos. 3,212,932 and 3,558,725. British Pat. No. 1,209,960 and Russian Pat. No. 167,845, 1965, contain related disclosure.

The prior art processes have not been employed to any great extent on a commercial scale because they are economically unsound. For example, where the xylose-rich solutions are obtained from wood chips following the prior art processes, the solutions have been so impure that several costly process steps, are required before xylose can be recovered or before a solution of appropriate purity is obtained that can be hydrogenated to form xylitol.

In accordance with the present invention, an improved method for the production of xylose from pentosan-containing, specifically xylan-containing raw materials has now been developed in which a pentose-rich solution obtained by acid hydrolysis of a pentosan-containing raw material is purified by mechanical filtration and ion exclusion techniques for color removal and desalting. This solution is then subjected to chromatographic fractionation to obtain a highly purified solution of xylose. The xylose solution of high purity may be used as a source of xylose in aqueous solution form, or xylose may be crystallized therefrom. Alternately, where xylitol is desired, the solution may be hydrogenated to produce xylitol, a preferred way of accomplishing the chromatographic fractionation step is by passing the solution through a column of an alkaline earth metal salt of a polystyrene sulfonate cation exchange resin cross-coupled with di-vinyl benzene, the column having a height of from about 2.5 to about 5 meters.

One of the advantages of the process of this invention is that it provides a solution of xylose of sufficiently high purity to warrant hydrogenation thereof to xylitol on a commercial scale if desired.

Materials used as the raw materials from which the pentosan-rich solutions are obtained are preferably lignocellulose materials including wood of various species of trees, such as birch and beach. Also useful are oat hulls, corn cobs and stalks, coconut shells, almond shells, straw, bagasse and cotton seed hulls. Where wood is used, it is preferably subdivided into wood chips, shavings, saw dust and the like.

DESCRIPTION OF THE DRAWINGS

The invention will be further described with reference to the drawings, in which:

Referring to FIG. 1, the raw materials may be hydrolyzed in the first stage of the present invention by following any of the well known procedures in the art. Suitable procedures described in the literature include those given in U.S. Pat. Nos. 2,734,836; 2,759,856; 2,801,939; 2,974,067 and 3,212,932. The important considerations in selecting the appropriate method of hydrolysis is that a maximum yield of pentoses be obtained and that the resulting pentose-rich solution be neutralized using materials which do not cause serious deterioration of sugars, such as sodium hydroxide. Where the pentose material is obtained by methods other than acid hydrolysis, the step of desalting by ion exclusion described below may not be required.

The next stage in the process where a hydrolysis product is used is that of the purification of the hydrolysis product. The purification stage comprises two main steps; one is removal of the salt, sodium sulfate, and the major part of organic impurities and coloring bodies by ion-exclusion techniques, while the second step accomplishes final color removal. The ion exclusion technique removes salt from the solution and similar processes have been used in the sugar industry for the purification of molasses. Suitable processes are described for example in U.S. Pat. Nos. 2,890,972 and 2,937,959.

Upon completion of the salt removal step the solution still contains some organic and inorganic impurities. These are removed by the color removal step by treating the impure solutions with ion exchange systems consisting of a strong cation exchanger followed by a weak anion exchanger and then followed by a step of passing the solution through an adsorbant or activated carbon bed. These methods are also known in the sugar industry. One such procedure is described for example in U.S. Pat. No. 3,558,725. Other pertinent disclosures of this feature include J. Stamberg and V. Valter: Entfarbungsharze, Akademie Verlag Berlin 1970; P. Smit: Ionenaustauscher und Adsorber bei der Herstellung und Reinigung von Zuckern, Pektinen und verwandten Stoffen. Akademie Verlag Berlin 1969; J. Hassler: Activated carbon; Leonard Hill London 1967.

Figure 2:
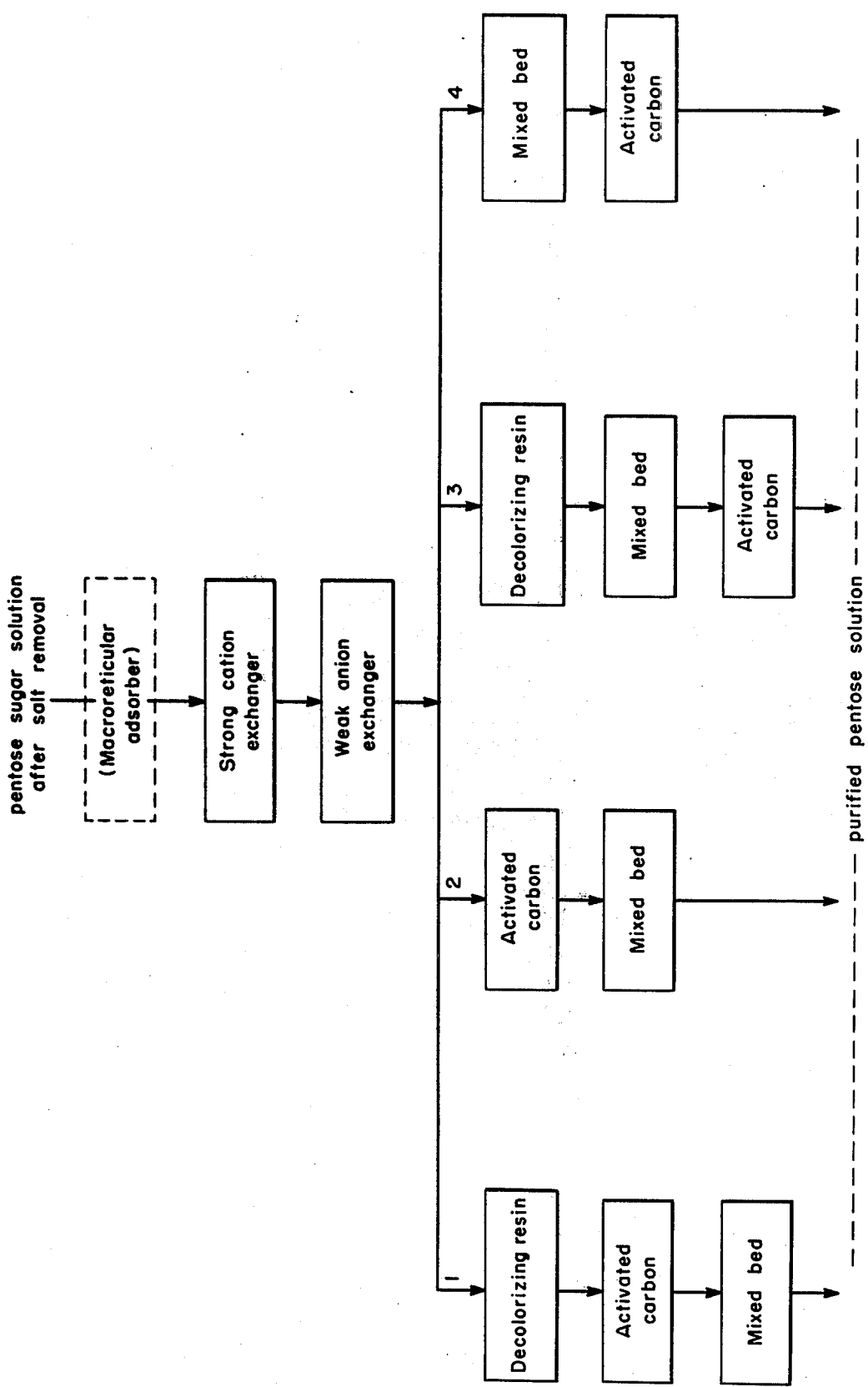
FIG. 2 is a flow diagram showing four possible procedures for purifying pentose sugar solutions in accordance with the invention.

As shown in FIG. 2 the purification step may be further improved where necessary by the addition of a step which uses a synthetic macroreticular adsorbant such as Amberlite XAD 2 to remove organic impurities. The macroreticular adsorbant can be used in the purification stage immediately following the ion exclusion step but prior to the cation exchanger as shown in FIG. 2. Alternatively, it can be the final step of the purification stage.

FIG. 2 shows four alternate schemes for accomplishing the purification stage of the process of the present invention. Selection of one of these alternate schemes will depend upon the nature and level of the impurities present in the solution and upon the composition of the solution undergoing purification.

Figure 1:
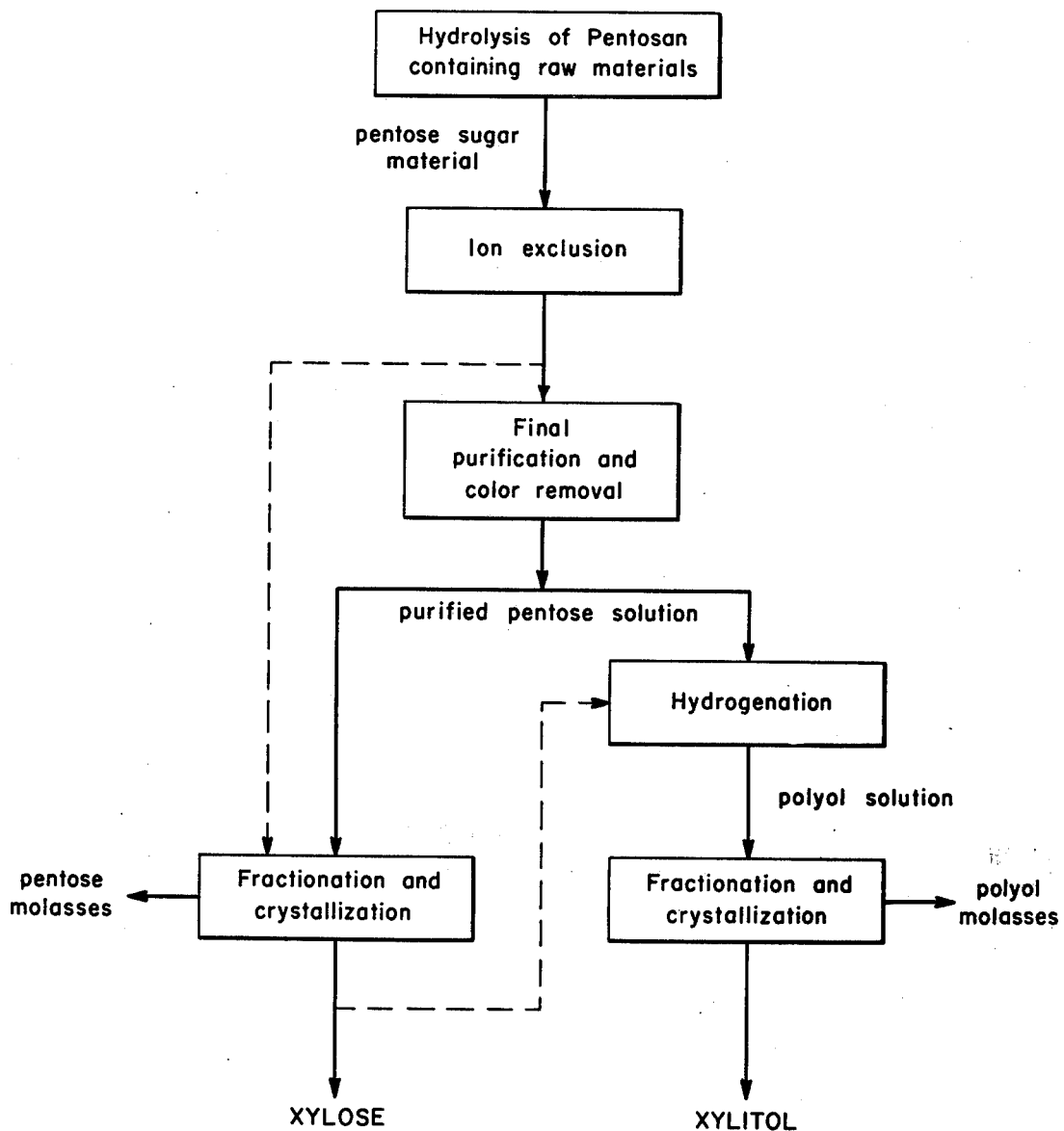
FIG. 1 is a flow diagram showing generally the processes of the present invention.

The purified pentose solution obtained in the purification stage may then be used for the recovery of xylose as shown in FIG. 1 by chromatographic fractionation to obtain a solution with a high purity with respect to xylose, followed by crystallization. The pentose molasses, made up of unselected fractions, may be subjected to further chromatographic fractionation procedures to recover one or more of the other sugars present therein. Alternatively, it can be used as a source of carbohydrate in fermentation processes.

Figure 3:
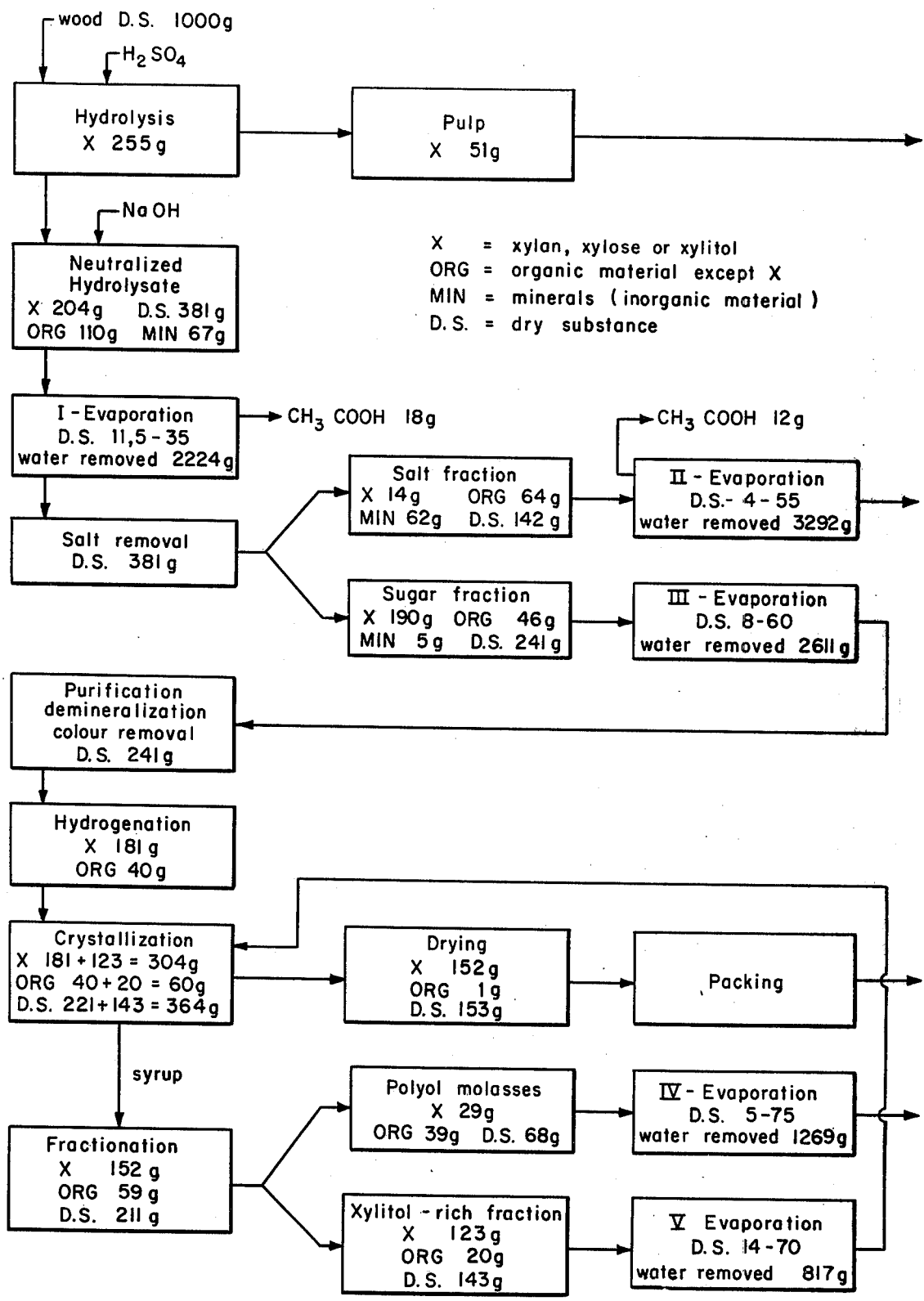
FIG. 3 is a flow diagram with material balance scheme for a process of preparing xylose and xylitol from wood chips.

Alternatively, where xylitol is desired, the purified pentose solution is hydrogenated and treated according to t;e procedure outlined in FIG. 3. The hydrogenation process is conducted in a manner similar to the hydrogenation of glucose to sorbitol. A suitable process is found in an article by W. Schnyder entitled "The Hydrogenation of Glucose to Sorbitol with Raney Nickel Catalyst", Dissertation at the Polytechnical Institute of Brooklyn, 1962.

EXAMPLE I

A xylose-rich solution obtained as shown in FIG. 1 may be purified advantageously by chromatographic fractionation and subsequent crystallization. The purified pentose solution contains several sugars in addition to xylose and the solution can be greatly enriched with respect to xylose by utilizing chromatographic fractionation techniques. In carrying out this example, a chromatographic column comprising a strongly acid cation exchanger in the form of a sulfonated polystyrene, cross-coupled with 3.5% of di-vinyl benzene, in strontium form, is contained in a column 1.0 meter high and 9.4 centimeters in diameter. The resin is submerged with water. A pentose solution containing 25% solids and having the following composition was used as the feed solution:

| Sugar | Percent, Dry Solids Basis |
| --- | --- |
| Xylose | 73 |
| Arabinose | 6.1 |
| Mannose | 9.0 |
| Galactose | 5.1 |
| Glucose | 6.8 |

The solution was uniformly fed across the top of the column at the rate of 27 ml per minute until a total of 60 grams of solids are fed to the column. The first 108 ml of material through the column comprising mostly the water originally in the column, are discarded. An analysis of the fractions obtained thereafter is given in Table II below.

Table II

| Fraction | Grams of: | | | | |
| --- | --- | --- | --- | --- | --- |
| | Glucose | Xylose | Mannose | Galactose | Arabinose |
| 1 | 0.2 | — | — | — | — |
| 2 | 0.35 | — | — | — | — |
| 3 | 0.75 | 0.2 | — | — | — |
| 4 | 1.1 | 0.9 | — | — | — |
| 5 | 1.0 | 4.4 | 0.05 | — | — |
| 6 | 0.45 | 9.05 | 0.3 | 0.1 | — |
| 7 | 0.2 | 11.65 | 0.6 | 0.3 | — |
| 8 | 0.05 | 9.8 | 1.0 | 0.6 | — |
| 9 | — | 5.0 | 1.3 | 0.9 | — |
| 10 | — | 1.85 | 1.05 | 0.6 | 0.5 |
| 11 | — | 0.75 | 0.7 | 0.35 | 0.8 |
| 12 | — | 0.2 | 0.35 | 0.15 | 1.1 |
| 13 | — | — | 0.05 | 0.05 | 0.8 |
| 14 | — | — | — | — | 0.4 |
| 15 | — | — | — | — | 0.1 |

By combining fractions 6, 7 and 8, applicants obtained a solution having a xylose purity of 89%.

This xylose-rich fraction can be used in the production of a pure crystalline xylose. Alternatively the xylose-rich solution obtained by combining fractions 6, 7 and 8 may be hydrogenated as shown in FIG. 1 to obtain a relatively pure xylitol solution. It is additionally possible to crystallize the xylose from the impure solution, such as the feed solution used above in this example, and to thereafter fractionate the sugars which remain in the syrup by chromatographic procedures using ion exchanger resins. The xylose-rich fraction is recirculated to the crystallization step. It is also possible to obtain other pentoses and hexoses from corresponding fractions or the balance of the fractions may be combined into a pentose molasses.

EXAMPLE II

Birch wood in the form of chips is used to prepare xylose and xylitol. A material balance scheme for this example is given in FIG. 3 of the drawings.

In accordance with the process of this example, sufficient birch wood chips to provide 1,000 grams of dry substance are hydrolyzed with sulfuric acid to provide a mixture of hydrolysate and pulp which contains totally 225 grams of xylose. The pulp, containing 51 grams of xylan is removed from the hydrolysate and either discarded or used for some other purpose. The balance of the hydrolysate containing 204 grams of xylose is neutralized with sodium hydroxide to provide a hydrolysate containing 204 grams of xylose, 110 grams of organic material exclusive of xylose and 67 grams of inorganic material. The hydrolysate is then heated to drive off unwanted acidic acid and water, and then subjected to a step of salt removal by ion exclusion and purification by passing the solution through successive beds of strong cation exchanger and weak anion exchanger. As shown in the drawing, 14 grams of xylose together with a major portion of the inorganic material and some of the organic material are removed and discarded in the salt fraction. The sugar fraction, containing most of the xylose together with a portion of the organic impurities and a small amount of inorganic impurities are again subjected to an evaporation step to remove additional quantities of water.

The concentrated sugar solution thus obtained is passed through a color removal step and activated carbon bed The thus purified solution, containing 181 grams of xylose together with 40 grams of organic material, is hydrogenated. After hydrogenation, the solution is heated to evaporate a portion of the water, and from the concentrated solution xylitol is crystallized.

EXAMPLE III

A xylose-rich solution obtained by hydrolysis of birch wood, followed by salt removal and color removal procedures as described above, was further purified by chromatographic fractionation on an ion exchange resin column in accordance with the procedure described below. The composition of the solids content of the xylose-rich solution as determined by gas chromatographic analysis, was:

| Sugar | Percent |
| --- | --- |
| Arabinose | 6 |
| Xylose | 78 |
| Mannose | 7.5 |
| Galactose | 5 |
| Glucose | 4.5 |

The resin employed was a strongly acid cation exchanger, sulfonated polystyrene cross-coupled with 3.5% of di-vinyl benzene, the resin being in calcium form. The resin had a mean particle size of 0.32 mm. The separation was conducted at a temperature of 49° C. The column was 350 cm in height and had a diameter of 22.5 cm. The column was submerged in water. The xylose-rich solution was fed uniformly across the column at a rate of 17 liters per hour. The total amount fed to the column was four kilograms of solids, as a solution having a solids content of 26%.

The first effluent from the column, in the amount of 88 liters and mostly comprising water, was discarded. Thereafter, successive fractions were collected and analyzed, with the following results:

|          | Dry Substance, Grams |        |         |           |           |
|----------|---------|--------|---------|-----------|-----------|
| Fraction | Glucose | Xylose | Mannose | Galactose | Arabinose |
| 1        | 8       | 41     | —       | —         | —         |
| 2        | 91      | 165    | —       | —         | —         |
| 3        | 75      | 497    | —       | —         | —         |
| 4        | 8       | 704    | 25      | —         | —         |
| 5        | —       | 720    | 91      | 25        | —         |
| 6        | —       | 580    | 124     | 83        | —         |
| 7        | —       | 289    | 58      | 41        | 8         |
| 8        | —       | 83     | 7       | —         | 66        |
| 9        | —       | 8      | —       | —         | 99        |
| 10       | —       | —      | —       | —         | 66        |

Fractions 3 through 6 were combined to provide 35 liters of a xylose-rich solution which had the following analysis:

| Sugar     | Grams         |
|-----------|---------------|
| Arabinose | —             |
| Xylose    | 2483 (= 85%)  |
| Mannose   | 240           |
| Galactose | 108           |
| Glucose   | 83            |

EXAMPLE IV

A xylose-rich solution obtained by hydrolysis of birch wood followed by salt removal and color removal procedures as described above was further purified by chromatographic fractionation on an ion exchange resin column as described below. The composition of the solids content of the xylose-rich solution, as determined by gas chromatographic analysis, was:

| Sugar     | Percent |
|-----------|---------|
| Arabinose | 6.5     |
| Xylose    | 77      |
| Mannose   | 8       |
| Galactose | 4       |
| Glucose   | 4.5     |

The resin employed was a strongly acid cation exchanger, sulfonated polystyrene cross-coupled with 3.5% of di-vinyl benzene, the resin being in strontium form. The resin had a mean particle size of 0.32 mm. The separation was conducted at a temperature of 51° C. The column was 350 cm in height and had a diameter of 22.5 cm. The column was submerged in water. The xylose-rich solution was fed uniformly across the column at the rate of 15 liters per hour and the total amount of solids supplied to the column was four kilograms, in the form of a solution having a solids content of 28%.

The first effluent from the column, in the amount of 88 liters and comprising mostly water, was discarded. Thereafter, successive fractions were collected and analyzed, with the following results:

|          | Dry substance, Grams |        |         |           |           |
|----------|---------|--------|---------|-----------|-----------|
| Fraction | Glucose | Xylose | Mannose | Galactose | Arabinose |
| 1        | 8       | 41     | —       | —         | —         |
| 2        | 83      | 157    | —       | —         | —         |
| 3        | 75      | 447    | —       | —         | —         |
| 4        | 7       | 662    | —       | —         | —         |
| 5        | —       | 696    | 33      | 8         | —         |
| 6        | —       | 580    | 91      | 40        | —         |
| 7        | —       | 331    | 108     | 75        | 25        |
| 8        | —       | 124    | 66      | 33        | 91        |
| 9        | —       | 41     | 17      | 7         | 99        |
| 10       | —       | 10     | —       | —         | 41        |

Fractions 3 through 6 were combined to provide 35 liters of a xylose-rich solution which had the following analysis:

| Sugar     | Grams         |
|-----------|---------------|
| Arabinose | —             |
| Xylose    | 2385 (= 90%)  |
| Mannose   | 124           |
| Galactose | 48            |
| Glucose   | 82            |

We claim:

1. A method for the production of xylose from a pentose-rich solution obtained by acid hydrolysis of a pentosan-containing raw material which comprises the steps of:
   a. removing suspended solids from the solution by mechanical filtration;
   b. removing inorganic salts and the major portion of organic impurities and color by ion exclusion;
   c. removing the balance of color and other organic impurities by treating the solution with a material selected from the group consisting of an ion exchange resin and activated carbon; and
   d. fractionating the solution thus obtained by ion exchange chromatographic techniques to provide a xylose solution of high purity.

2. The method of claim 1 wherein the xylose solution of high purity is crystallized and the crystals separated from the balance of the solution to provide crystals of substantially pure xylose.

3. The process of claim 1 wherein step (d) is accomplished by
   a. providing a column of a salt of a polystyrene sulfonate cation exchange resin cross-coupled with di-vinyl benzene;
   b. submerging the column of resin in water;
   c. feeding the pentose-rich solution having a dry material content of 25 to 55% by weight in uniform supply to the resin surface in the column at a flow rate of 0.2 to 1.5 cubic meters per hour per square meter of the cross-section of the resin column; and
   d. recovering successively from the downstream side of the resin bed
      1. a dilute fraction containing mostly water but also containing other pentoses and a low level of xylose,
      2. an intermediate fraction having a high level of xylose and small amounts of other pentoses, and
      3. a final fration containing other pentoses and a minor amount of xylene.

4. A method for the production of xylose from xylan-containing raw material which comprises the steps of:
   a. hydrolyzing the raw material with acid to produce a pentose-rich solution,
   b. neutralizing the solution with alkali, c. filtering the solution to remove solids suspended therein,
d. passing the solution through a bed selected from the group consisting of an ion exclusion column and a column of activated carbon to remove inorganic salts and the major portion of organic impurities,
e. then passing the solution through an ion exchange resin column to remove the balance of color and other oganic impurities, and
f. fractionating the solution thus obtained by passing it through a chromatographic column of ion exchange resin to obtain a xylose solution of high purity and a pentose molasses.

5. The method of claim 4, wherein the raw material is birch wood chips, and wherein the fractionating of step (f) is accomplished by a. providing a column of a salt of a polystyrene sulfonate cation exchange resin cross-coupled with divinyl benzene;
b. submerging the column of resin in water;
c. feeding the pentose-rich solution having a dry material content of 25 to 55% by weight in uniform supply to the resin surface in the column at a flow rate of 0.2 to 1.5 cubic meters per hour per square meter of the cross-section of the resin column; and
d. recovering successively from the downstream side of the resin bed
   1. a dilute fraction containing mostly water but also containing other pentoses and a low level of xylose,
   2. an intermediate fraction having a high level of xylose and small amounts of other pentoses, and
   3. a final fraction containing other pentoses and a minor amount of xylose.

* * * * *

UNITED STATES PATENT OFFICE
CERTIFICATE OF CORRECTION

Patent No. 4,075,406          Dated February 21, 1978

Inventor(s) ASKO J. MELAJA and LAURI HAMALAINEN

It is certified that error appears in the above-identified patent and that said Letters Patent are hereby corrected as shown below:

Col. 4, line 15, after "xylitol" insert --in accordance with the process of the present invention --;
Col. 6, line 62, "fration" should read --fraction--;
Col. 6, line 63, "xylene" should read --xylose--.

Signed and Sealed this

Eleventh Day of July 1978

[SEAL]

Attest:

RUTH C. MASON
Attesting Officer

DONALD W. BANNER
Commissioner of Patents and Trademarks